United States Patent
Leiniger et al.

(10) Patent No.: US 8,945,236 B2
(45) Date of Patent: Feb. 3, 2015

(54) LINER HAVING AN INTEGRATED ELECTRODE

(75) Inventors: Andreas Leiniger, Birkungen (DE); Jens Volkmar, Gerblingerode (DE); Mathias Görth, Seulingen (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 0 days.

(21) Appl. No.: 13/521,771

(22) PCT Filed: Jan. 17, 2011

(86) PCT No.: PCT/DE2011/000055
§ 371 (c)(1),
(2), (4) Date: Jul. 12, 2012

(87) PCT Pub. No.: WO2011/088822
PCT Pub. Date: Jul. 28, 2011

(65) Prior Publication Data
US 2012/0296445 A1    Nov. 22, 2012

(30) Foreign Application Priority Data
Jan. 20, 2010   (DE) .......................... 10 2010 005 462

(51) Int. Cl.
*A61F 2/72* (2006.01)
*A61F 2/78* (2006.01)

(52) U.S. Cl.
CPC .................. *A61F 2/7812* (2013.01); *A61F 2/72* (2013.01); *A61F 2002/7818* (2013.01)
USPC ............................................. 623/25; 623/36

(58) Field of Classification Search
USPC ............................... 623/24, 25, 32–37, 57–65
See application file for complete search history.

(56) References Cited

U.S. PATENT DOCUMENTS

| | | | |
|---|---|---|---|
| 5,443,525 | A | 8/1995 | Laghi |
| 5,571,208 | A | 11/1996 | Caspers |
| 7,670,385 | B2 | 3/2010 | Klein |
| 2009/0216339 | A1 | 8/2009 | Hanson et al. |
| 2010/0030341 | A1 | 2/2010 | Dietl et al. |
| 2010/0318195 | A1 | 12/2010 | Kettwig et al. |

FOREIGN PATENT DOCUMENTS

| | | |
|---|---|---|
| DE | 102005021412 A1 | 11/2006 |
| DE | 202006007460 U1 | 9/2007 |
| DE | 102007035409 A1 | 1/2009 |
| DE | 202010005472 U1 | 9/2010 |

OTHER PUBLICATIONS

PCT International Search Report for International Application No. PCT/DE2011/000055, mailed Jun. 20, 2011.

*Primary Examiner* — Bruce E Snow
(74) *Attorney, Agent, or Firm* — Holland & Hart

(57) ABSTRACT

The invention relates to a liner that is intended to be pulled over an amputation stump, is made of an electrically non-conducting material, has a form that is adapted or that adapts to the amputation stump, has an inner wall (7) that lies against the skin of the amputation stump, and is provided with at least one electrode (11), which is arranged between the skin of the amputation stump and the outside of the liner (1) in order to transmit electrical signals, a high level of wearing comfort is ensured along with reliable transmission of the electrical signals in that at least one conducting section (6) is integrated into the material of the liner (1) in the area of the electrodes (11), the at least one conducting section forming a uniform and consistently oriented inner wall together with the non-conducting material of the liner (1).

20 Claims, 2 Drawing Sheets

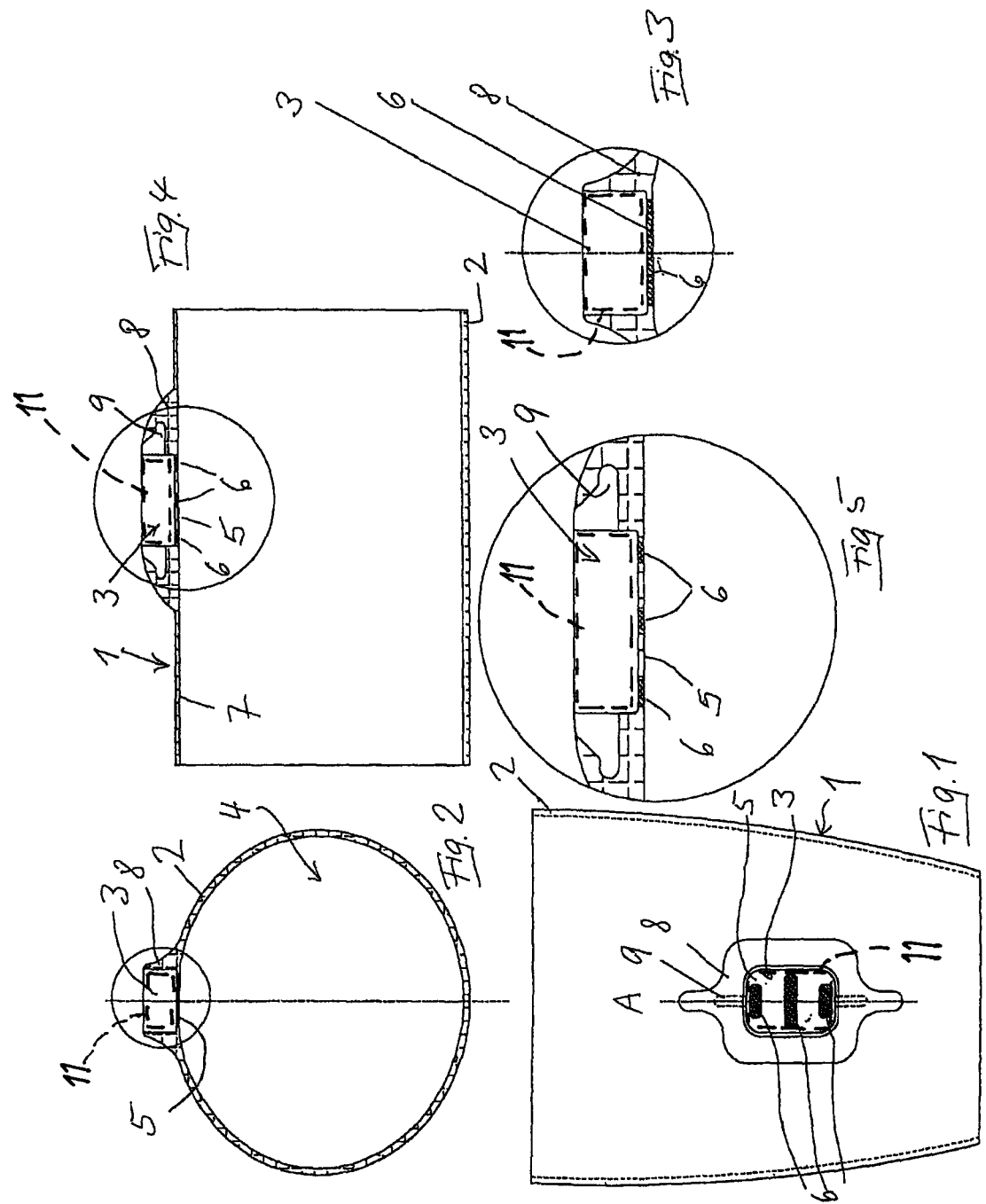

LINER HAVING AN INTEGRATED ELECTRODE

TECHNICAL FIELD

The invention relates to a liner which is intended to be pulled over an amputation stump, is made of an electrically non-conducting material, has a shape that is adapted or that adapts to the amputation stump, has an inner wall coming to lie against the skin of the amputation stump, and is provided with at least one electrode which is arranged to transmit electrical signals between the skin of the amputation stump and the outside of the liner.

BACKGROUND

Liners of the type in question here have a certain wall thickness and function as a cushioning intermediate layer that is formed between the amputation stump and the inner wall of a prosthesis socket and is adapted or adapts to the amputation stump. The prosthesis socket is part of a prosthesis that replaces the amputated part of an extremity of the patient.

Transmission of electrical signals between the amputation stump and the outside of the liner may be considered for a number of reasons. Thus, it may be useful to transmit electrical signals from the skin of the amputation stump to the outside, in order to control the function of the prosthesis. In this case, the electrodes can be myoelectric electrodes which pick up muscle contraction signals at suitable points of the amputation stump, as a result of which corresponding prosthetic limbs can be controlled. Myoelectric control of prostheses is known particularly for prosthetic arms and hands but can also be used for prosthetic legs and feet.

It may also be useful to electrically determine the surface resistance of the skin of the amputation stump by measuring a current flow between two or more electrodes or electrode sections. It is in this way possible, for example, to determine whether the skin of the amputation stump within the liner transpires, which can adversely affect the fit of the liner on the amputation stump, hence the fit of the prosthesis. It is also possible to use electrodes to determine the contact pressure of the amputation stump on the inner wall of the liner, so as to be able to react, for example, to mass shrinkage of the amputation stump during the period the prosthesis is worn.

Conversely, it may be useful to transmit electrical signals from the outside of the liner to the skin of the amputation stump, for example in order to excite a muscle contraction of the amputation stump when the prosthesis wearer is located for some time in a passive position, for example a seated position.

U.S. Pat. No. 5,443,525 discloses a liner that is intended to receive myoelectric electrodes. For this purpose, a non-metallic, flexible and soft pad, in which a large number of discrete conducting electrodes are located, is bonded into a window of the prosthesis socket. The liner is preferably made of silicone, a non-conducting flexible plastic. The electrodes can be formed from a mixture of silicone and carbon or of silicone and silver, the electrodes being surrounded in each case by non-conducting silicone. The electrode arrangement is thus bonded via the pad onto the inner face of the liner and is accessible through the window of the liner, such that the myoelectric signals picked up by the electrodes can be conveyed through the window to the outside for evaluation or control. This arrangement is expensive to produce and provides limited wearing comfort. In addition, the window of the liner requires special sealing if the liner, as is often the case, has to be made airtight, in order to hold the liner on the amputation stump with the aid of an underpressure created in the interior of the liner. The underpressure has to be maintained by the liner counter to the weight of the moved prosthesis.

SUMMARY

The object of the present invention is therefore to design a liner of the type mentioned at the outset in such a way as to ensure a high degree of wearing comfort and reliable contact by the electrodes.

This object is achieved, according to the invention, by a liner of the type mentioned at the outset being characterized in that at least one conducting section is integrated into the material of the liner in the area of the electrode and, together with the non-conducting material of the liner, forms a uniform and continuously oriented inner wall.

The liner according to the invention thus has at least one conducting section for an electrode, which section is part of the material of the liner, such that a uniform and continuous inner wall is present that does not differ from the inner wall of a liner without electrodes. The material of the liner is preferably a polymer, for example silicone. The conducting section has preferably been inserted into the material before polymerization to completion, such that, upon complete polymerization of the material of the liner, the conducting section is connected to the latter to form a uniform part, resulting in the continuous, smooth inner wall.

It is advantageous if the conducting section is made from the material of the liner, which material has been made electrically conductive by additives, as is known in principle from U.S. Pat. No. 5,443,525, for example. It is also possible, although not essential, that the conducting section is polymerized to completion together with the material of the liner.

The conducting section of the liner can itself be designed as an electrode, for example in contact with a lead via which a detected electrical signal is conveyed to a control system, or an electrical signal acting as an excitation signal for the amputation stump is transmitted to the skin thereof.

In a preferred embodiment, however, the conducting section of the liner serves as a contact maker for an electrode, which is applied to the outside of the conducting section. In this case, the conducting section preferably forms a thin wall of a recess that is formed in the material of the liner and that receives the electrode. This permits precise and safe positioning of the electrode at a predetermined location of the liner.

The recess can have an edge formed by a material thickening, as a result of which, on the one hand, the insertion of the electrode is stabilized and, on the other hand, the electrode is optionally protected over its entire thickness. The edge can be provided with undercuts for receiving correspondingly protruding edges of the electrode, such that the edge at the same time serves for securely fastening the electrode in the seat. The undercuts are preferably applied in such a way that the electrode is pressed with a certain prestressing against the conducting section, in order to ensure that reliable contact is made.

The electrode is preferably provided with a lead that carries the electrical signal and that is routed at least in part in the material of the liner. For this purpose, the liner can have incisions which are open to the outside and into which the lead can be placed. Alternatively, it is possible that at least one lead running from the recess to a suitable location of the liner, preferably to a closed end of the liner, is already integrated into the liner at the time of production of the latter. In this case, a suitable contacting device for the electrode has to be provided in the seat. This device can be formed, in the simplest case, from a protruding, non-insulated part of the lead that can be connected to the electrode inserted into the seat, for example by a plug connection, as is customary for the attachment of lamp cables, by screw contact terminals or also by soldering.

The liner according to the invention can be produced in a conventional production method that is only slightly modified, and therefore the liner can be designed with the electrodes, or to receive electrodes, without great additional outlay or considerable additional costs.

BRIEF DESCRIPTION OF THE DRAWINGS

The invention is explained in more detail below on the basis of illustrative embodiments depicted in the drawing, in which:

FIG. 1 shows a plan view of a section of a liner with a seat for an electrode;

FIG. 2 shows a cross section through the liner according to FIG. 1;

FIG. 3 shows an enlarged detail A from FIG. 2;

FIG. 4 shows a longitudinal section through the liner according to FIG. 1;

FIG. 5 shows an enlarged view of the detail B from FIG. 4;

DETAILED DESCRIPTION

Figure 6:
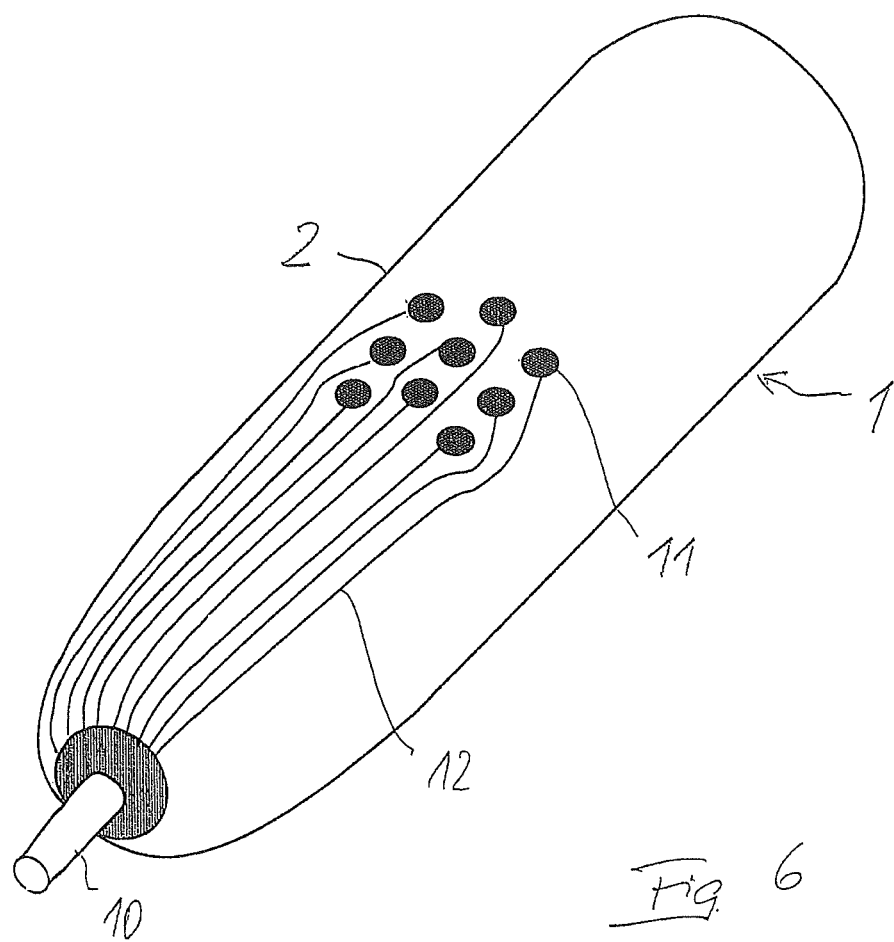
FIG. 6 shows a perspective view of a liner which is closed at the distal end and which has a plurality of electrodes or seats for electrodes, and with connecting leads that are formed in the liner and that run to a connector plug mounted on the distal end of the liner.

The section of a liner as shown in FIGS. 1 to 5 reveals that it is designed with a seamlessly closed wall 2 and, as is customary, narrows in a funnel shape toward a distal end. A seat 3 in the form of a radially outwardly open chamber is formed in the material of the wall 2 and is closed off from an interior 4 of the liner by a thin wall part 5 serving as the base of the recess 3. Three conducting sections 6 are located in the wall part 5 and are separated at a distance from one another by the non-conducting material of the liner 1. The conducting sections are formed in one piece with the material of the wall part 5, such that a smooth and continuous inner wall 7 is also present in the area of the seat 3, as can be seen in particular from FIGS. 3 and 5.

FIGS. 2 to 5 show that the seat 3 is delimited by an edge 8, which is formed by a material thickening of the wall 2 of the liner 1.

FIG. 1 shows that the edge 8 extends as a substantially rectangular frame along the axial direction A and that the three conducting sections 6 are arranged one after another in the axial direction A. The cross section depicted in FIGS. 2 and 3 runs through the middle conducting section, while the longitudinal sections in FIGS. 4 and 5 are shown in the plane of the axial direction A in FIG. 1.

FIGS. 4 and 5 also show that undercuts 9 are formed in the axial direction A in the edge 8, into which undercuts 9 it is possible to insert correspondingly shaped and protruding edges of an electrode, by virtue of the flexibility of the material of the wall 2 and of the edges 8. In this way, the edge 8 at the same time serves to fasten an electrode safely and securely in the seat 3.

Thus, in the embodiment shown in FIGS. 1 to 5, conducting sections 6 serve as conducting transmission means between the skin of the amputation stump, introduced into the liner 1, and an electrode, introduced into the seat 3. This embodiment is preferable to directly designing the conducting sections 6 themselves as electrodes.

FIG. 6 shows a perspective view of the complete funnel-shaped liner 1, which is closed at its distal end and has there a schematically illustrated multi-pole connector plug 10. A number of electrodes 11 are introduced into the wall 2 of the liner and, in accordance with the illustration in FIGS. 1 to 5, can be inserted into corresponding seats 3. From the electrodes 11, connecting leads 12 extend axially in the wall 2 of the liner as far as the plug 10 at the distal end of the liner 1. The connecting leads 12 are preferably introduced into the wall 2 of the liner 1 during the production of the latter, i.e. pre-produced along with the liner 1. This is particularly advantageous if the electrodes 11 are not connected directly to the associated connecting lead 12 but can instead be brought into contact with the connecting lead 12 by insertion into a seat 3. The electrical contact of the electrode 11 to the skin of the patient takes place in each case via the conducting sections 6 in the thin wall part 5 of the seat 3.

It is not essential for a single electrode 11 to be inserted into the seat 3. Instead, the electrode 11 can also consist of different electrode sections, which are flush with the several conducting sections 6. It is thus possible, for example, to measure the current flow between two conducting sections 6 in order to determine the conductivity of the skin of the amputation stump resting on the inner wall 7.

Similarly, numerous measurements can be carried out on the skin of the amputation stump. In particular, the liner 1 according to the invention can also be used to record myoelectric signals from the amputation stump.

Another possible use involves transmitting electrical stimulation signals from the outside of the liner 1 to the skin of the amputation stump inserted into the liner 1.

The liner according to the invention has a smooth and continuous inner wall 7 and, in terms of its wearing properties, does not differ from conventional liners designed without electrodes.

The invention claimed is:

1. A liner having an interior, a closed end, and an open end, and which is intended to be pulled over an amputation stump to position the amputation stump in the interior, is made of an electrically non-conducting material, has a shape that is adapted or that adapts to the amputation stump, has an inner wall coming to lie against the skin of the amputation stump, has at least one seat accessible along an outer wall of the liner, and is provided with at least one electrode which is positioned in the at least one seat, wherein at least one conducting section is formed integrally with the material of the liner in the area of the at least one electrode seat and, together with the non-conducting material of the liner, forms a uniform, uninterrupted and continuous inner surface of the inner wall, wherein the at least one electrode and the at least one conducting section are electrically connected to each other when the at least one electrode is positioned in the at least one seat, and are configured to transmit electrical signals between the skin of the amputation stump and an outside of the liner.

2. The liner as claimed in claim 1, wherein the material of the liner is a polymer, and the conducting section is integrated into the material before polymerization to completion.

3. The liner as claimed in claim 2, wherein the conducting section is made from the material of the liner, which material has been made electrically conductive by additives.

4. The liner as claimed in claim 3, wherein the conducting section is polymerized to completion together with the material of the liner.

5. The liner as claimed in claim 1, wherein the conducting section includes the at least one electrode.

6. The liner as claimed in claim 1, wherein the at least one electrode is applied to the outside of the conducting section.

7. The liner as claimed in claim 6, wherein the conducting section forms a thin wall of the at least one seat that is formed in the material of the liner.

8. The liner as claimed in claim 7, wherein the at least one seat has an edge formed by a material thickening.

9. The liner as claimed in claim 8, wherein the edge is provided with undercuts for receiving correspondingly protruding edges of the at least one electrode.

10. The liner as claimed in claim 1, wherein the at least one electrode is provided with a lead that carries the electrical signal and that is routed at least in part in the material of the liner.

11. A liner having an interior cavity, a closed end, and an open end, the liner being configured to be pulled over an amputation stump to position the amputation stump inside the interior cavity, the liner comprising an electrically non-conducting material, being of a shape that is adapted or that adapts to the amputation stump, having an inner wall coming to lie against the skin of the amputation stump, having at least one seat formed in and accessible along an outer wall of the liner, having at least one electrode positioned in the at least one seat, and having at least one conducting section formed integrally with the material of the liner in the area of the at least one seat and, together with the non-conducting material of the liner, forms a uniform, uninterrupted and continuous inner surface of the inner wall, wherein the at least one electrode and the at least one conducting section are electrically connected to each other and configured to transmit electrical signals between the skin of the amputation stump and an outside of the liner.

12. The liner as claimed in claim 11, wherein the material of the liner is a polymer, and the at least one conducting section is inserted into the material before polymerization to completion.

13. The liner as claimed in claim 11, wherein the at least one conducting section is made from the material of the liner, which material has been made electrically conductive by additives.

14. The liner as claimed in claim 13, wherein the at least one conducting section is polymerized to completion together with the material of the liner.

15. The liner as claimed in claim 11, wherein the at least one conducting section forms a thin wall of a recess that is formed in the material of the liner and that receives the at least one electrode.

16. The liner as claimed in claim 15, wherein the recess has an edge formed by a material thickening.

17. The liner as claimed in claim 16, wherein the edge is provided with undercuts for receiving correspondingly protruding edges of the at least one electrode.

18. The liner as claimed in claim 17, wherein the at least one electrode is provided with a lead that carries the electrical signal and that is routed at least in part in the material of the liner.

19. A liner, comprising:
a closed end;
an open end;
a sidewall having an inner surface forming an interior cavity sized to receive an amputation stump through the open end, the inner surface being arranged in contact with skin of the amputation stump, the sidewall comprising an electrically non-conducting material;
at least one seat formed in and accessible along an outer surface of the sidewall;
at least one electrode positioned in the at least one seat,
at least one conducting section positioned adjacent to the at least one electrode and formed integrally with the electrically non-conducting material, the at least one conducting section, together with the non-conducting material, forming a uniform, uninterrupted and continuous inner surface of the sidewall;
wherein the at least one electrode and the at least one conducting section are electrically connected and are configured to transmit electrical signals between the skin of the amputation stump and an outer surface of the liner.

20. The liner as claimed in claim 19, wherein the material of the liner is a polymer, and the conducting section is inserted into the material before polymerization to completion.

* * * * *